(12) United States Patent
Chen et al.

(10) Patent No.: US 11,819,408 B2
(45) Date of Patent: Nov. 21, 2023

(54) LEAFLET POSITIONING AND FIXING CLIP AND NARROW-ENVIRONMENT ORIENTATION SYSTEM THEREOF

(71) Applicant: Shanghai ConFlow MedTech Co., Ltd., Shanghai (CN)

(72) Inventors: Xiumin Chen, Shanghai (CN); Baicheng Hu, Shanghai (CN); Qing Li, Shanghai (CN)

(73) Assignee: SHANGHAI CONFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 18/012,228

(22) PCT Filed: Jul. 29, 2022

(86) PCT No.: PCT/CN2022/108914
§ 371 (c)(1),
(2) Date: Dec. 22, 2022

(87) PCT Pub. No.: WO2023/087780
PCT Pub. Date: May 25, 2023

(65) Prior Publication Data
US 2023/0190468 A1    Jun. 22, 2023

(30) Foreign Application Priority Data
Nov. 19, 2021 (CN) .......................... 202111410789.4

(51) Int. Cl.
*A61F 2/24* (2006.01)
(52) U.S. Cl.
CPC .... *A61F 2/2454* (2013.01); *A61F 2220/0016* (2013.01)

(58) Field of Classification Search
CPC ......... A61F 2/2454–2/2466; A61F 2220/0016; A61F 2210/0014; A61F 2230/0043;
(Continued)

(56) References Cited

U.S. PATENT DOCUMENTS

2004/0049207 A1   3/2004 Goldfarb et al.
2016/0287387 A1*  10/2016 Wei ...................... A61F 2/2454
(Continued)

FOREIGN PATENT DOCUMENTS

CN   111867486 A   10/2020
CN   211723546 U   10/2020
(Continued)

*Primary Examiner* — Paul B Prebilic
(74) *Attorney, Agent, or Firm* — Bayramoglu Law Offices LLC (57) ABSTRACT

A leaflet positioning and fixing clip and a narrow-environment orientation system thereof are provided. The clip includes a fixing element, a lower gripping arm assembly sleeved outside the fixing element, an upper gripping arm assembly sleeved outside the lower gripping arm assembly, a pull rope controlling the upper gripping arm assembly to move, and an occlusive film attached below the lower gripping arm assembly. The upper gripping arm assembly includes an upper central fixing plate and upper gripping arms radially distributed around the upper central fixing plate. The lower gripping arm assembly includes a lower central fixing plate and lower gripping arms. There are at least two upper gripping arms mated with at least two lower gripping arms to form grippers for gripping a tricuspid valve. The occlusive film is stably positioned in a center of the tricuspid valve through the grippers.

20 Claims, 6 Drawing Sheets

(58) Field of Classification Search
CPC ...... A61F 2230/0093; A61F 2250/0006; A61F 2250/0039
See application file for complete search history.

(56) References Cited

U.S. PATENT DOCUMENTS

| | | | |
|---|---|---|---|
| 2018/0325671 A1* | 11/2018 | Abunassar | A61B 17/08 |
| 2019/0142589 A1* | 5/2019 | Basude | A61F 2/2463 |
| | | | 623/2.11 |
| 2019/0321166 A1 | 10/2019 | Freschauf et al. | |
| 2022/0142780 A1* | 5/2022 | Zhang | A61F 2/2466 |

FOREIGN PATENT DOCUMENTS

| | | |
|---|---|---|
| CN | 112741711 A | 5/2021 |
| CN | 114099076 A | 3/2022 |
| CN | 216777299 U | 6/2022 |
| WO | 2010098804 A1 | 9/2010 |

* cited by examiner

LEAFLET POSITIONING AND FIXING CLIP AND NARROW-ENVIRONMENT ORIENTATION SYSTEM THEREOF

CROSS REFERENCE TO THE RELATED APPLICATIONS

This application is the national phase entry of International Application No. PCT/CN2022/108914, filed on Jul. 29, 2022, which is based upon and claims priority to Chinese Patent Application No. 202111410789.4, filed on Nov. 19, 2021, the entire contents of which are incorporated herein by reference.

TECHNICAL FIELD

The present application provides a leaflet positioning and fixing clip and a narrow-environment orientation system thereof and belongs to the technical field of medical devices.

BACKGROUND

The heart is composed of four chambers: left atrium, left ventricle, right atrium, and right ventricle, which are connected to the main arteries, vena cava, pulmonary trunk, and pulmonary veins. There is a valve between the ventricle and the atrium. The valve between the left atrium and the left ventricle is referred to as the mitral valve, and the valve between the right atrium and the right ventricle is referred to as the tricuspid valve.

Tricuspid regurgitation (TR) is a common heart valve disease. In severe cases, TR can lead to decreased cardiac output and systemic congestion, and even death. Surgery is currently the mainstream method to treat TR, but it has the disadvantages of large incisions, many complications, high mortality, etc. Therefore, considering the limitations of surgery, it is necessary to develop a TR treatment method with a small incision, simple operation, and fewer complications. For this purpose, interventional treatment is very promising.

The United States patent US20040049207A1, entitled "Fixation Device and Methods for Engaging Tissue," uses minimally invasive or intravascular interventional surgery to achieve a breakthrough in gripping and fixation of the heart valve and solve the problem of valve regurgitation. For a long time afterward, the treatment solution developed rapidly due to its technical advantages. At present, gripping the heart valve for regurgitation treatment has become one of the mainstream techniques. However, in the conventional gripping solution, on the one hand, the connection between the upper and lower gripping arms easily becomes a weak point, and the high requirements of the multi-branch structure for the production process lead to a decline in product yield. On the other hand, the existing clip lacks a positioning point, making it hard to mate with the in-vivo positioning structure. At present, the most developed interventional repair technology of tricuspid valves adopt edge-to-edge repair, such as Abbott's MitraClip (PCT/USA 2009/068023) and Edwards PASCAL (US 2019/0321166A1) as typical representatives. The clip device grips and draws the leaflets to eliminate and reduce valve regurgitation. It has been widely used in clinical practice and has become one of the most commonly used treatment techniques for mitral regurgitation. However, it is hard for the grippers to close, which is not convenient for delivery from outside the body. In addition, since there are only two grippers, only two leaflets can be gripped, and the gripped area is limited. There are also attempts to use the clip device for TR treatment in clinical practice, but it is difficult to operate due to the need to implant multiple grippers.

SUMMARY

An objective of the present application is to provide a leaflet fixing gripper, which is convenient to operate and deliver, solves the problem of weak connection between upper and lower gripping arms, and can be combined to effectively treat TR.

To achieve the above objective, the present application adopts the following technical solutions. A first aspect of the present application provides a leaflet positioning and fixing clip, including a fixing element, and lower gripping arms and upper gripping arms that are superimposed in sequence on a side wall of the fixing element.

The upper gripping arms are pre-shaping structures, and each include a fixed segment and a free segment that form a first pre-shaping angle; and the upper gripping arms each are provided with an actuator configured to close and abut the free segment on the fixed segment.

The lower gripping arms are pre-shaping structures, and each include a fixed segment and a free segment that form a second pre-shaping angle.

The first pre-shaping angle is greater than the second pre-shaping angle. The fixing element is provided with a connecting member that is detachably connected to a delivery system.

In the case of an external force being exerted, the free segment is bent and deviated from the fixed segment. When the external force is withdrawn or weakened, the free segment is restored to form the pre-shaping angle. This is called pre-shaping. The angle herein refers to an internal angle. The connecting member may be a threaded hole or an anchoring hole, which is mated with the delivery system to deliver the whole device to the desired location. The upper gripping arms and the lower gripping arms may be fixed to the fixing element by a screw or a bolt or may be bonded to the outer side of the fixing element.

Preferably, the upper gripping arms and the lower gripping arms each are a memory metal strip structure, which allows the free segment to switch between an unbent state and a pre-shaped state relative to the fixed segment. The free segment of the upper gripping arm and the free segment of the lower gripping arm form a gripper, which tends to grip in the case of no external force being applied to grip a leaflet and fix the gripper and an accessory thereof. The first pre-shaping angle formed between the free segment and the fixed segment of the upper gripping arm is greater than the second pre-shaping angle formed between the free segment and the fixed segment of the lower gripping arm. The free segment of the upper gripping arm in the pre-shaped state is released to compress the free segment of the lower gripping arm to create a gripping force.

Preferably, at least two grippers are radially distributed around the fixing element. The fixed segments of the upper gripping arm and the lower gripping arm of each gripper are superimposed, such that the free segments of the upper gripping arm and the lower gripping arm of each gripper achieve stable gripping. Two grippers are combined for mitral valve repair, and three grippers are combined for tricuspid valve repair.

Preferably, at least two of the upper gripping arms are connected to an upper central fixing plate, and the lower gripping arms having the same quantity as the upper gripping arms are connected to a lower central fixing plate. The upper central fixing plate and the lower central fixing plate are superimposed in sequence and are fixed to the top of the fixing element. The upper gripping arms are radially distributed around the upper central fixing plate, and the lower gripping arms are radially distributed around the lower central fixing plate. The fixed segments of the upper gripping arm and the lower gripping arm of each gripper are superimposed, such that the free segments of the upper gripping arm and the lower gripping arm of each gripper achieve stable gripping.

The central fixing plate is angled with the gripping arm and sleeved outside the fixing element in a Q shape. Because the shape of the outer wall of the fixing element is mated with the Q shape, the positioning and fixation of the fixing element and the gripping arm are realized.

Preferably, the free segment of the upper gripping arm is provided with barbs facing the corresponding lower gripping arm. The upper gripping arm and the lower gripping arm stably grip the leaflet through the barbs.

Preferably, the free segment of the upper gripping arm is connected to the actuator in the form of a pull rope. A pulled end of the pull rope is connected to the top of the fixing element and extends in vitro to control the free segment of the upper gripping arm to open and close. The connection method of the pull rope is not limited. Specifically, the pull rope may be bonded, welded, or may be passed through a pull ring provided at the free segment. In this way, the upper gripping arm is actuated by the pull rope to move away from or close to the free segment of the lower gripping arm. When the pull rope is pulled up, the free segment of the upper gripping arm is moved toward the upper central fixing plate. The free segment of the lower gripping arm returns to the pre-shaped state. The leaflet can be inserted into the angled space between the free segment of the upper gripping arm and the free segment of the lower gripping arm. After the leaflet is inserted into the angled space, the pull rope is released. The free segment of the upper gripping arm restores its memory attribute and moves close to the free segment of the lower gripping arm to grip the leaflet.

Preferably, an occlusive film is filled between each two adjacent lower gripping arms. The occlusive disc film is generally a polymer film or a biological tissue film. Specifically, the occlusive film is stitched at the edge of the lower gripping arm or filled as a whole for partial tricuspid valve replacement.

Preferably, the occlusive film is a disc film fixed at the bottom of the fixing element and attached below all the lower gripping arms to fill a gap between each two adjacent lower gripping arms. When the lower gripping arms recover from an unbent state to a pre-shaped state, the occlusive film opens like an umbrella to cover the gap between each two adjacent lower gripping arms to play an occlusive role.

Further, a fine memory metal wire frame is inserted into the occlusive film from the surface of the occlusive film. The frame formed by the fine memory metal wires increases the overall toughness of the occlusive disc film, makes the occlusive disc film not easily deformed by the impact of the blood flow, and assists the positioning of the lower gripping arm.

Preferably, an upper surface of the occlusive film is partially connected to a lower surface of the lower gripping arm through attachment points. The area of the attachment points or a region enclosed by the attachment points on the lower surface of the lower gripping arm is smaller than the area of the lower surface of the lower gripping arm.

The attachment points can be fixedly connected by stitching, bonding, hot melting, screwing, etc.

Further, the attachment points of the lower gripping arm for attaching the occlusive film are located at an axis of the lower gripping arm.

The special arrangement of the attachment points at the axis makes the flow guide adapted to a physiological curve.

Preferably, the occlusive film between each two adjacent lower gripping arms is in a slack state.

That is, the surface of the occlusive film is not tight after the lower gripping arm is opened. In other words, the length of the occlusive film between the closest attachment points of each two adjacent lower gripping arms is greater than the linear distance between the attachment points.

Preferably, the occlusive film between each two adjacent lower gripping arms is elastic.

Through the design of the elastic or slack occlusive disc film, the blood flowing from one side impacts the disc film from one side and pushes the disc film to the edge of the lower gripping arm and the tricuspid valve. The blood flowing from the other side impacts the disc film from the other side and pushes the disc film away from the lower gripping arm from a region outside the attachment points to guide the blood flow. The design realizes a large opening degree on one side.

Preferably, the fixing element is a prism with sides, which have the same quantity as the grippers and are closely fitted to the inner sides of the lower gripping arms. The outer sides of the lower gripping arms are closely fitted to the inner sides of the upper gripping arms.

The special configuration of the fixing element can maximally limit the rotation of the lower gripping arms relative to the fixing element.

Further, a side of the fixing element is provided with slots for accommodating and limiting the lower gripping arms. The slot limits the rotation of the lower gripping arm relative to the fixing element and reduces the protrusion from the surface.

In some possible implementations, the upper central fixing plate and the lower central fixing plate are fixed to the fixing element using a threaded connection, that is, by a screw, which passes through the upper central fixing plate and the lower central fixing plate in sequence and is fixed to the fixing element.

In some possible implementations, the fixing element, the lower central fixing plate, and the upper central fixing plate form an integrated central structure, and all the upper gripping arms and lower gripping arms serve as branch arms of the central structure and are integrally connected to the central structure.

A second aspect of the present application further provides a narrow-environment orientation system of the leaflet positioning and fixing clip. In the clip, the free segment of the upper gripping arm has three switchable states relative to the fixed segment thereof: the unbent state, the pre-shaped state, and a closed state. In the unbent state, the free segment and the fixed segment form a straight line and are accommodated in a catheter for delivery of the clip. In the pre-shaped state, the free segment tends to move away from or close to the fixed segment to achieve a pre-shaping angle, that is, the free segment and the fixed segment form an L-shaped structure with the first pre-shaping angle. In the closed state, the free segment is actuated by an external force to abut on the fixed segment.

The free segment of the lower gripping arm has two states relative to the fixed segment: the unbent state and the pre-shaped state. In the unbent state, the free segment and the fixed segment form a straight line and are accommodated in the catheter to ease delivery of the entire clip. In the pre-shaped state, the free segment tends to move away from or close to the fixed segment to achieve a pre-shaping angle, that is, the free segment and the fixed segment form an L-shaped structure with the second pre-shaping angle. In the above solution, the upper gripping arm and the lower gripping arm of the clip are accurately pre-shaped to ensure reliable connection and stable gripping of the upper gripping arm assembly and the lower gripping arm assembly, thus reducing the difficulty of the production process and improving the yield.

In actual use, multiple grippers are combined for reliable tricuspid valve repair. When the occlusive film is present, the grippers are firmly located in the center of the tricuspid valve, which can effectively reduce the regurgitation in the center of the tricuspid valve and achieve partial valve replacement. The upper gripping arm and the lower gripping arm are made of elastic memory metals, so they are compressible and can be delivered through a small delivery system to achieve vascular implantation and reduce the surgical incision.

Taking partial tricuspid valve replacement as an example, the specific procedure is as follows. The grippers are sent to the center of the tricuspid valve in the right heart via the veins by a delivery catheter. The pull ropes of all the upper gripping arms are tightened to close the upper gripping arms. All the lower gripping arms are opened to enter the pre-shaped state. The pull ropes of all the upper gripping arms are tightened to maintain the closed state of the upper gripping arms. The angle and position of the fixing element are adjusted through the delivery device to place the lower gripping arms below the leaflet. The pull ropes are then loosened to release the upper gripping arms. The opening angles of the upper gripping arms are adjusted by the pull ropes to move the upper gripping arms close to the lower gripping arms to capture the leaflet. During the gripping process, the position of the fixing element can be continuously adjusted to facilitate the capture of the leaflet. After the capture and gripping of the leaflet are completed, the device is separated from the delivery system, such that the whole device stays stably in the center of the tricuspid valve. The occlusive film swings toward the atrial side during systole. At this time, the lower gripping arms and the tricuspid valve together limit the swing amplitude of the occlusive film to prevent TR at the center of the tricuspid valve. During diastole, the occlusive film is only pulled from the attachment points and can swing to the right ventricle at a relatively large amplitude to guide blood flow to the right ventricle. In this way, partial tricuspid valve replacement is achieved.

Reference Numerals: 1. upper gripping arm assembly; 11. upper gripping arm; 111. barb; 112. pull ring; 2. lower gripping arm assembly; 21. lower gripping arm; 211. slot; 3. fixing element; 31. upper central fixing plate; 32. lower central fixing plate; 4. screw; 5. bolt; and 6. disc film; 7. actuator.

DETAILED DESCRIPTION OF THE EMBODIMENTS

To make the present disclosure more understandable, the preferred embodiments of the present disclosure are described in detail below by referring to the drawings.

Figure 1:
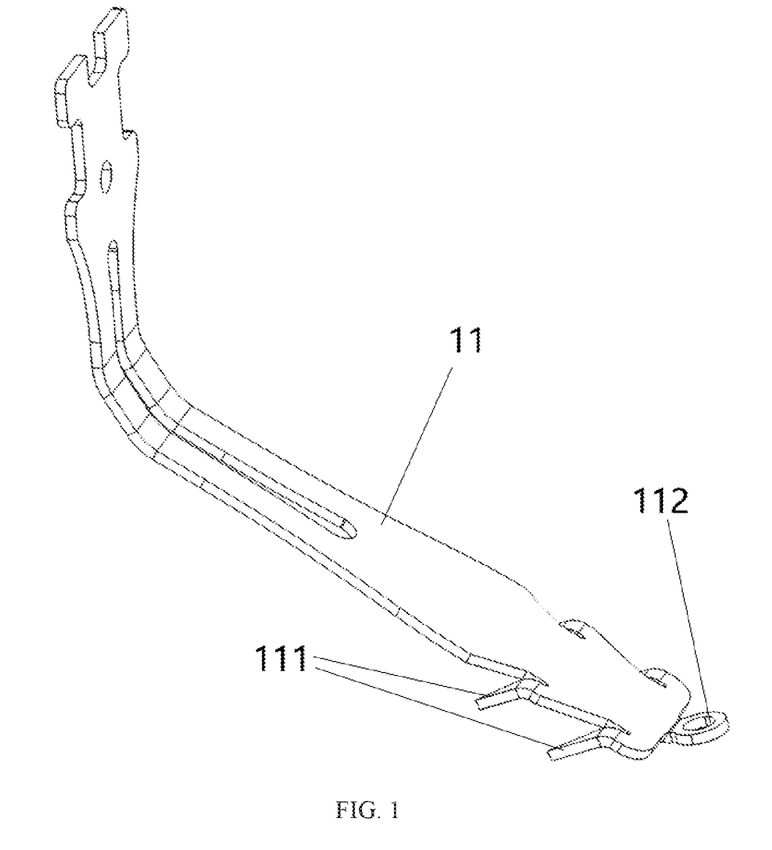
FIG. 1 shows an upper gripping arm of a clip in a pre-shaped state according to an embodiment of the present application.
Figure 3:
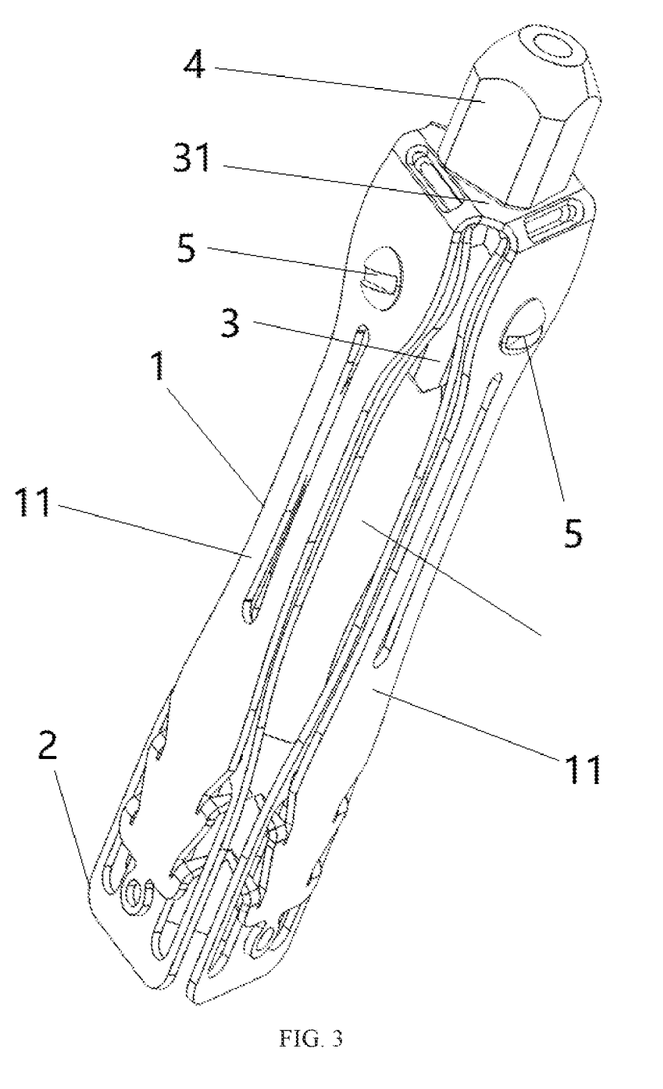
FIG. 3 shows the entire clip in an initial state according to an embodiment of the present application.
Figure 6:
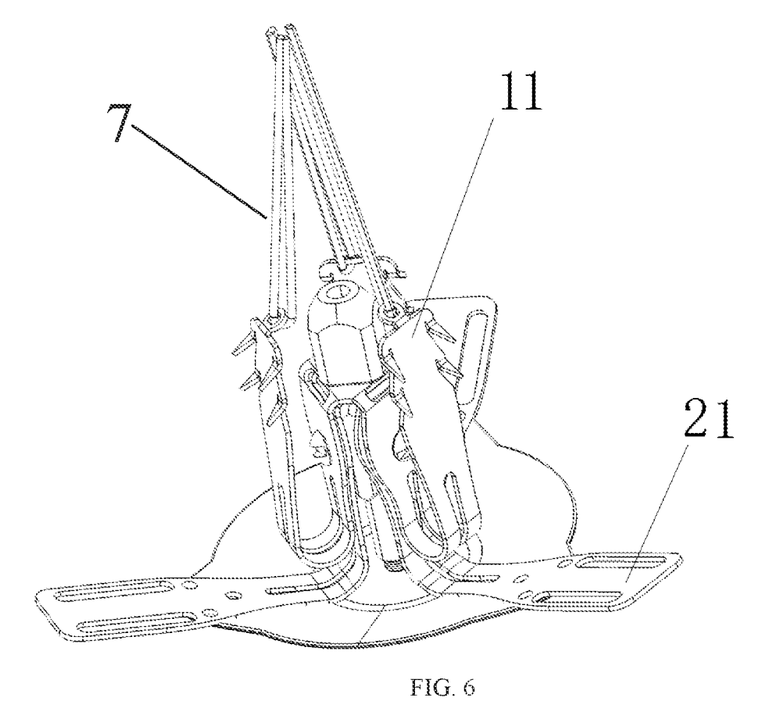
FIG. 6 shows the entire clip controlled by pull ropes for gripping according to an embodiment of the present application.

The present application provides a clip for positioning and fixing a membranous tissue. The clip includes upper gripping arm assembly 1 and lower gripping arm assembly 2. The upper gripping arm assembly 1 is an integrated structure, which includes an upper central fixing plate and at least two upper gripping arms 11. In some possible implementations, there may also be three or more upper gripping arms 11. The structure of the upper gripping arm 11 is shown in FIG. 1. The upper gripping arm 11 is a pre-shaping structure, including a fixed segment and a free segment. The fixed segment of the upper gripping arm 11 is fixedly connected to the upper central fixing plate. The free segment of the upper gripping arm 11 has two states: an unbent state and a pre-shaped state. In the unbent state, the free segment and the fixed segment form a straight line (in one plane, as shown in FIG. 3). In the pre-shaped state, the free segment is bent (as shown in FIG. 1). When the free segment is bent, it forms a pre-shaping angle called a first pre-shaping angle with the fixed segment. Under the action of an external force, the free segment moves close to the fixed segment. When there is no external force, the free segment tends to return to the pre-shaped state. That is, when the external force is withdrawn or weakened, the free segment tends to recover to form the first pre-shaping angle with the fixed segment. The free segment of the upper gripping arm 11 is provided with barbs 111 and pull ring 112. The barbs 111 are configured to capture a leaflet, and the pull ring 112 is connected to an actuator 7. In some possible implementations, the actuator 7 is in the form of a rope. A rope passes through the pull ring 112 to control the bending and unbending of the free segment of the upper gripping arm 11. When the pull rope is pulled, the free segment of the upper gripping arm 11 is controlled in a closed state (as shown in FIG. 6). There is no limit to the connection form of the pull rope. The pull rope may be fixed to the free segment directly by bonding or welding, avoiding the need to provide the pull rope ring separately.

Figure 2:
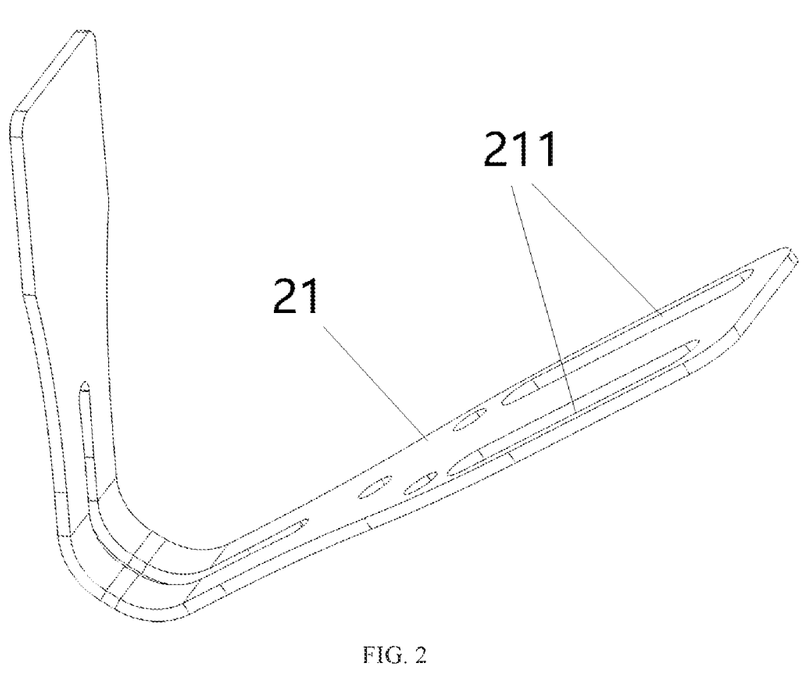
FIG. 2 shows a lower gripping arm of the clip in a pre-shaped state according to an embodiment of the present application.

The lower gripping arm assembly 2 is also an integrated structure, which includes a lower central fixing plate and lower gripping arms 21 having the same quantity as the upper gripping arms 11. The lower gripping arm 21 is also a pre-shaping structure, including a fixed segment and a free segment. The fixed segment of the lower gripping arm 21 is fixedly connected to the lower central fixing plate. The free segment of the lower gripping arm 21 has two states: an unbent state and a pre-shaped state. In the unbent state, the free segment and the fixed segment form a straight line (as shown in FIG. 3). In the pre-shaped state, the free segment is bent. When the free segment is bent, it forms a pre-shaping angle called a first pre-shaping angle with the fixed segment. As shown in FIG. 2, the lower gripping arm 21 is provided with slots 211 which are mated with the barbs 111 for the barbs 111 to pass through. The first pre-shaping angle is greater than the second pre-shaping angle. The free segment of the upper gripping arm 11 and the free segment of the lower gripping arm 21 form a gripper. Since the first pre-shaping angle is greater than the second pre-shaping angle, when there is no external force exerted, the free segment of the upper gripping arm 11 tends to compress the free segment of the lower gripping arm 21, such that they play a gripping role. The pull rope is configured to drive the free segment of the upper gripping arm 11 to move away from or close to the free segment of the lower gripping arm 21. When the pull rope is pulled up, the free segment of the upper gripping arm 11 is moved upward and away from the free segment of the lower gripping arm 21. The free segment of the lower gripping arm 21 returns to the pre-shaped state when there is no restraint. The leaflet can be inserted into the angled space between the free segment of the upper gripping arm and the free segment of the lower gripping arm. After the leaflet is inserted into the angled space, the pull rope is released. The free segment of the upper gripping arm 11 restores its memory attribute and moves close to the free segment of the lower gripping arm 21 to grip the leaflet.

In some possible embodiments, the upper gripping arm 11 and the lower gripping arm 21 are radially fixed around fixing element 3. The upper gripping arm 11 and the lower gripping arm 21 have the same number and correspond one by one to form a gripper. Two grippers are combined for mitral valve repair, and three grippers are combined for tricuspid valve repair. As shown in FIG. 3, there are three upper gripping arms and three lower gripping arms. The fixed segments of all the upper gripping arms 11 are fixedly connected to the upper central fixing plate to form the upper gripping arm assembly 1. The fixed segments of all the lower gripping arm 21 are fixedly connected to the lower central fixing plate to form the lower gripping arm assembly 2. The upper central fixing plate and the lower central fixing plate are provided with holes. The upper gripping arm assembly 1 and the lower gripping arm assembly 2 are sleeved on the top of the fixing element 3. Screws 4 successively penetrate screw holes in the top of the upper central fixed plate 31, the top of the lower central fixed plate 32, and the top of the fixing element 3 to position the upper gripping arm assembly 1, the lower gripping arm assembly 2 and the fixing element 3. The fixing element 3 is a triangular prism with three symmetrical sides corresponding to the three gripping arms. The sides of the fixing element 3 are closely fitted to the inner sides of the lower gripping arms 21, and the outer sides of the lower gripping arms 21 are closely fitted to the inner sides of the upper gripping arms to achieve a positioning purpose to avoid relative rotation after the screw 4 is fixed. In some possible implementations, the sides of the fixing element 3 each are provided with a slot for accommodating and limiting the lower gripping arm 21. The slot limits the rotation of the lower gripping arm 21 relative to the fixing element and reduces the protrusion from the surface. Alternatively, the three sides of the fixing element 3 as a central axis are provided with threaded holes for fixing the upper gripping arms and the lower gripping arms, and the fixed segments of the upper gripping arms and the lower gripping arms are directly fixed to the sides of the fixing element 3 through bolts 5. Alternatively, the fixing element 3, the lower central fixing plate, and the upper central fixing plate form an integrated central structure, and all the upper gripping arms and lower gripping arms serve as branch arms of the central structure and are integrally connected to the central structure.

Figure 4:
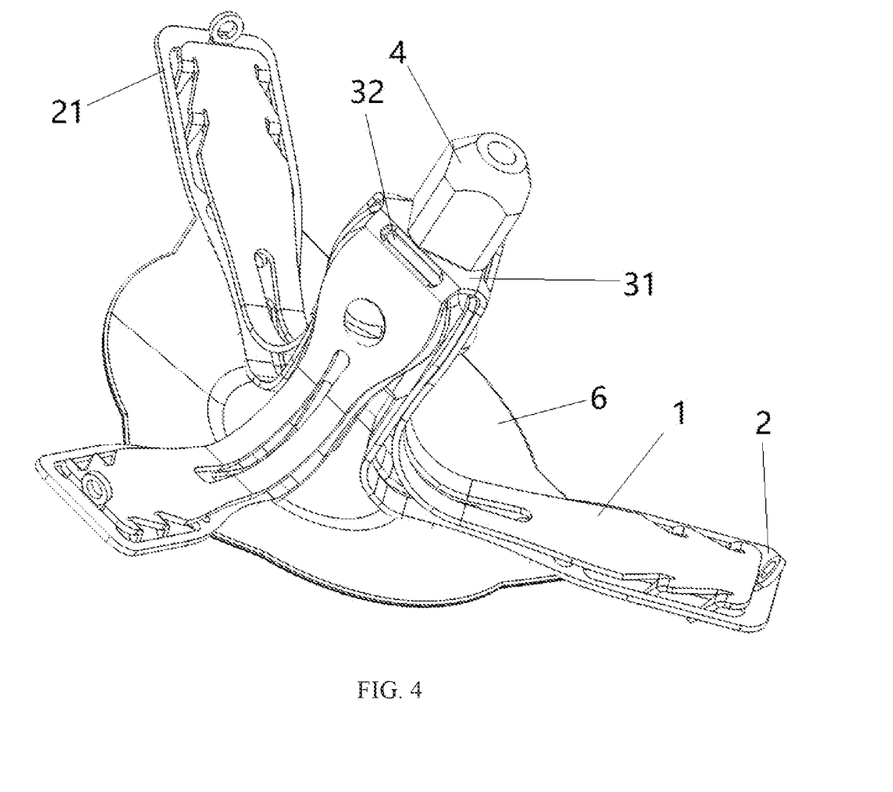
FIG. 4 shows the entire clip in a gripping state according to an embodiment of the present application.

The bottom of the fixing element 3 positioned away from the screw 4 is screwed with occlusive disc film 6. As shown in FIG. 4, the disc film 6 covers a gap between each two adjacent lower gripping arms 21. FIG. 4 shows the pre-shaped state of the upper gripping arm assembly 1 and the lower gripping arm assembly 2. The pre-shaping angle of the upper gripping arm 11 is greater than that of the lower gripping arm 21. Since the pre-shaping angles are inconsistent, the lower gripping arm assembly 2 and the upper gripping arm assembly 1 can grip tightly. The upper gripping arm 11 is provided with the barbs 111 and the pull ring 112. The barbs 111 are configured to capture the leaflet, and the pull ring 112 is configured for the pull rope to pass through. The pull rope controls the opening and closing of the upper gripping arm 11. The lower gripping arm 21 opposes the upper gripping arm 11, and the pre-shaping angles of the lower gripping arm 21 and the upper gripping arm 11 are staggered to ensure that each pair of gripping arms has a sufficient gripping force when combined. The lower gripping arm 21 is provided with the slots 211 that are mated with the barbs 111 and configured for the barbs 111 to pass through.

The occlusive disc film 6 covering the gap between each two adjacent lower gripping arms is generally a polymer film or a biological tissue film. Specifically, the disc film is stitched at the edge of the lower gripping arm or filled as a whole for partial tricuspid valve replacement. The disc film 6 is fixed at the bottom of the fixing element and attached below all the lower gripping arms to fill the gap between each two adjacent lower gripping arms. When the lower gripping arms recover from an unbent state to a pre-shaped state, the disc film 6 opens like an umbrella to cover the gap between each two adjacent lower gripping arms to play an occlusive role. A fine memory metal wire frame is inserted inside the disc film 6. The frame formed by the fine memory metal wires increases the overall toughness of the occlusive disc film, makes the occlusive disc film not easily deformed by the impact of the blood flow, and assists the positioning of the lower gripping arm. The upper surface of the disc film 6 is partially connected to a lower surface of the lower gripping arm through attachment points. The area of the attachment points or the area of the region enclosed by the attachment points on the lower surface of the lower gripping arm is smaller than the area of the lower surface of the lower gripping arm. The attachment points can be fixedly connected by stitching, bonding, hot melting, screwing, etc. The attachment points of the lower gripping arm for attaching the disc film 6 are located at an axis of the lower gripping arm to make the flow guide adapted to the physiological curve. The disc film 6 between each two adjacent lower gripping arms is in a slack (e.g., loose) state. That is, the surface of the disc film 6 is not tight after the lower gripping arm is opened. In other words, the length of the disc film 6 between the closest attachment points of each two adjacent lower gripping arms is greater than the linear distance between the attachment points. The disc film 6 between each two adjacent lower gripping arms is elastic. Through the design of the elastic or slack occlusive disc film, the blood flowing from one side impacts the disc film from one side and pushes the disc film to the edge of the lower gripping arm and the tricuspid valve. The blood flowing from the other side impacts the disc film from the other side and pushes the disc film away from the lower gripping arm from a region outside the attachment points to guide the blood flow. The design realizes a large opening degree on one side.

Figure 5:
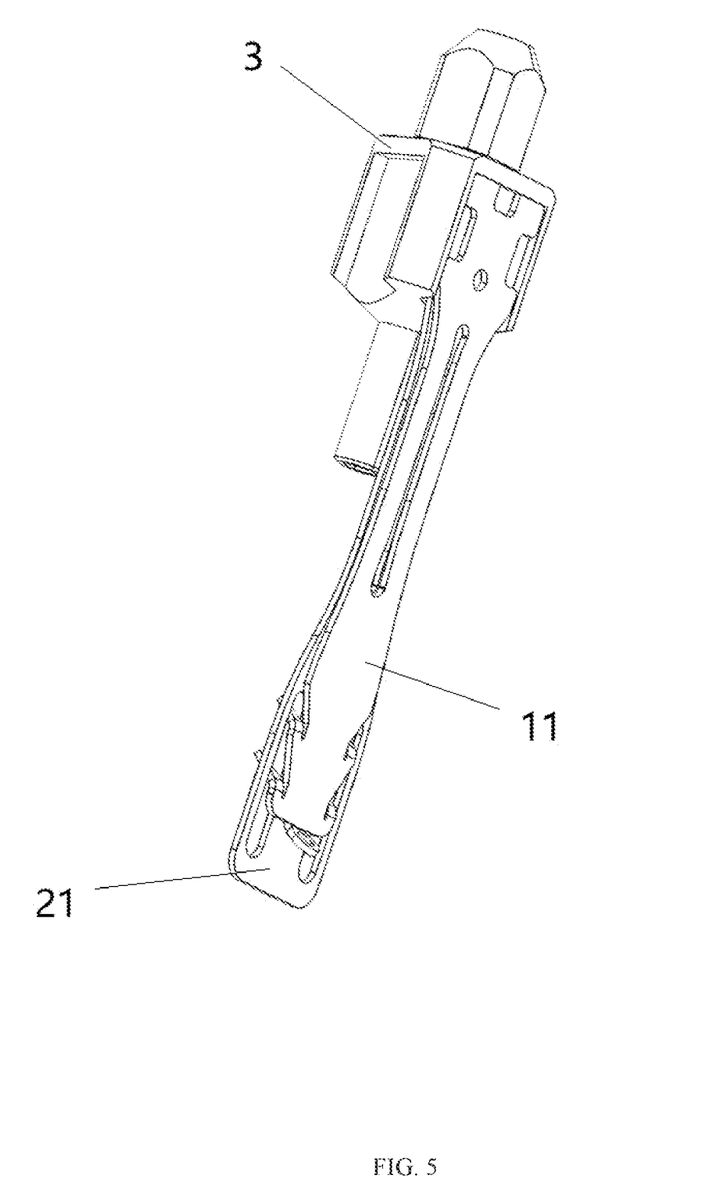
FIG. 5 shows a pair of upper gripping arm and a lower gripping arm of the clip in an initial state according to an embodiment of the present application.

In some possible embodiments, the sides of the fixing element 3 each are provided with a slot for accommodating the lower gripping arm to limit the lower gripping arm through the slot and avoid relative rotation of the lower gripping arm, as shown in FIG. 5.

In some possible embodiments, the fixing element 3, the lower central fixing plate 32, and the upper central fixing plate 31 form an integrated central structure, and all the gripping arms serve as branch arms of the central structure and are integrally connected to the central structure.

In some possible embodiments, the fixing element 3, the lower central fixing plate 32, and the upper central fixing plate 31 are formed separately and welded as a whole.

In some possible embodiments, the fixing element 3, the lower central fixing plate 32, and the upper central fixing plate 31 are bonded layer by layer and welded as a whole.

In some possible embodiments, the lower central fixing plate 32 and the upper central fixing plate 31 are fixed on the fixing element 3 by double bolts.

In some possible embodiments, the fixing element 3 may be provided with a positioning point to mate with the internal positioning structure (such as a guide wire terminal or an internal fixation point in the heart).

A working process of the clip in the present application is as follows: When the clip is delivered to the right ventricle, all the lower gripping arms 21 are opened, and the pull ropes of all the upper gripping arms 11 are tightened to maintain the upper gripping arms 11 in a closed state. The angle and position of the fixing element 3 are adjusted through the delivery device to place the lower gripping arms below the leaflet. The upper gripping arms are opened, and the opening angle of the upper gripping arms is adjusted through the pull ropes, such that the upper gripping arms move close to the lower gripping arms to capture the leaflet, as shown in FIG. 6. After the barbs 111 capture the leaflet, the pull ropes are completely released such that the upper gripping arms and the lower gripping arms tightly grip the leaflet. During the gripping process, the position of the fixing element 3 can be continuously adjusted to facilitate the capture of the leaflet. After the capture and gripping of the leaflet are completed, the fixing element 3 is separated from the delivery device, such that the clip stays stably at the designated position.

What is claimed is:

1. A leaflet positioning and fixing clip, comprising a fixing element, and lower gripping arms and upper gripping arms that are superimposed in sequence on a side wall of the fixing element, wherein
   the upper gripping arms are pre-shaping structures, and each comprise a fixed segment and a free segment that form a first pre-shaping angle; and the upper gripping arms each are provided with an actuator configured to close and abut the free segment on the fixed segment;
   the lower gripping arms are pre-shaping structures, and each comprise a fixed segment and a free segment that form a second pre-shaping angle; and
   the first pre-shaping angle is greater than the second pre-shaping angle; and the fixing element is provided with a connecting member that is detachably connected to a delivery system.

2. The leaflet positioning and fixing clip according to claim 1, wherein the upper gripping arms and the lower gripping arms each are a memory metal strip structure that allows the free segment to switch between an unbent state and a pre-shaped state relative to the fixed segment; and the free segment of the upper gripping arm and the free segment of the lower gripping arm form a gripper, which tends to grip in case of no external force to grip a leaflet and fix the gripper and an accessory thereof.

3. The leaflet positioning and fixing clip according to claim 2, wherein at least two grippers are radially distributed around the fixing element; and the fixed segments of the upper gripping arm and the lower gripping arm of each gripper are superimposed, such that the free segments of the upper gripping arm and the lower gripping arm of each gripper achieve stable gripping.

4. The leaflet positioning and fixing clip according to claim 1, wherein at least two of the upper gripping arms are connected to an upper central fixing plate, and lower gripping arms having a same quantity as the upper gripping arms are connected to a lower central fixing plate; the upper central fixing plate and the lower central fixing plate are superimposed in sequence and are fixed to a top of the fixing element; the upper gripping arms are radially distributed around the upper central fixing plate, and the lower gripping arms are radially distributed around the lower central fixing plate; and the fixed segments of the upper gripping arm and the lower gripping arm of each gripper are superimposed.

5. The leaflet positioning and fixing clip according to claim 4, wherein the upper central fixing plate and the lower central fixing plate are fixed to the fixing element using a threaded connection which passes through the upper central fixing plate and the lower central fixing plate in sequence and is fixed to the fixing element.

6. The leaflet positioning and fixing clip according to claim 4, wherein the fixing element, the lower central fixing plate, and the upper central fixing plate form an integrated central structure; and all the upper gripping arms and lower gripping arms serve as branch arms of the central structure and are integrally connected to the central structure.

7. The leaflet positioning and fixing clip according to claim 1, wherein a free segment of the upper gripping arm is provided with barbs, wherein the barbs face the lower gripping arm.

8. The leaflet positioning and fixing clip according to claim 1, wherein a free segment of the upper gripping arm is connected to the actuator in a form of a pull rope; and a pulled end of the pull rope is connected to a top of the fixing element and extends in vitro to control the free segment of the upper gripping arm to open and close.

9. The leaflet positioning and fixing clip according to claim 1, wherein an occlusive film is disposed between each two adjacent lower gripping arms.

10. The leaflet positioning and fixing clip according to claim 9, wherein the occlusive film is a disc film fixed at a bottom of the fixing element, and the occlusive film is attached below all the lower gripping arms to fill a gap between each two adjacent lower gripping arms; and when the lower gripping arms recover from an unbent state to a pre-shaped state, the occlusive film opens like an umbrella to cover the gap between each two adjacent lower gripping arms to play an occlusive role.

11. The leaflet positioning and fixing clip according to claim 9, wherein a fine memory metal wire frame is inserted into the occlusive film from a surface of the occlusive film.

12. The leaflet positioning and fixing clip according to claim 9, wherein an upper surface of the occlusive film is partially connected to a lower surface of the lower gripping arm through attachment points; and an area of the attachment points or a region enclosed by the attachment points on the lower surface of the lower gripping arm is smaller than an area of the lower surface of the lower gripping arm.

13. The leaflet positioning and fixing clip according to claim 12, wherein the attachment points of the lower gripping arm for attaching the occlusive film are located at an axis of the lower gripping arm.

14. The leaflet positioning and fixing clip according to claim 9, wherein the occlusive film between each two adjacent lower gripping arms is in a slack state.

15. The leaflet positioning and fixing clip according to claim 9, wherein the occlusive film between each two adjacent lower gripping arms is elastic.

16. The leaflet positioning and fixing clip according to claim 1, wherein the fixing element is a prism with sides, which have a same quantity as the lower gripping arms and are closely fitted to inner sides of the lower gripping arms; and outer sides of the lower gripping arms are closely fitted to inner sides of the upper gripping arms.

17. The leaflet positioning and fixing clip according to claim 1, wherein a side of the fixing element is provided with slots for accommodating and limiting the lower gripping arms.

18. A narrow-environment orientation system of the leaflet positioning and fixing clip according to claim 1, wherein
the free segment of the upper gripping arm has three switchable states relative to the fixed segment thereof: an unbent state, a pre-shaped state, and a closed state; in the unbent state, the free segment and the fixed segment form a straight line and are accommodated in a catheter for delivery of the entire clip; in the pre-shaped state, the free segment moves away from or close to the fixed segment to achieve a first pre-shaping angle; and in the closed state, the free segment is actuated by an external force to abut on the corresponding fixed segment; and
the free segment of the lower gripping arm has two states relative to the fixed segment: the unbent state and the pre-shaped state; in the unbent state, the free segment and the fixed segment form a straight line and are accommodated in the catheter for delivery of the entire clip; and in the pre-shaped state, the free segment moves away from or close to the fixed segment to achieve a second pre-shaping angle.

19. The narrow-environment orientation system according to claim 18, wherein in the leaflet positioning and fixing clip, the upper gripping arms and the lower gripping arms each are a memory metal strip structure that allows the free segment to switch between the unbent state and the pre-shaped state relative to the fixed segment; and the free segment of the upper gripping arm and the free segment of the lower gripping arm form a gripper, which tends to grip in case of no external force to grip a leaflet and fix the gripper and an accessory thereof.

20. The narrow-environment orientation system according to claim 19, wherein in the leaflet positioning and fixing clip, at least two grippers are radially distributed around the fixing element; and the fixed segments of the upper gripping arm and the lower gripping arm of each gripper are superimposed, such that the free segments of the upper gripping arm and the lower gripping arm of each gripper achieve stable gripping.

* * * * *